US009867629B2

(12) United States Patent
Hawkins

(10) Patent No.: US 9,867,629 B2
(45) Date of Patent: Jan. 16, 2018

(54) ANGIOPLASTY BALLOON

(71) Applicant: SHOCKWAVE MEDICAL, INC., Fremont, CA (US)

(72) Inventor: Daniel Hawkins, Fremont, CA (US)

(73) Assignee: SHOCKWAVE MEDICAL, INC., Fremont, CA (US)

( * ) Notice: Subject to any disclaimer, the term of this patent is extended or adjusted under 35 U.S.C. 154(b) by 727 days.

(21) Appl. No.: 14/445,314

(22) Filed: Jul. 29, 2014

(65) Prior Publication Data
US 2015/0039002 A1    Feb. 5, 2015

Related U.S. Application Data

(60) Provisional application No. 61/860,755, filed on Jul. 31, 2013.

(51) Int. Cl.
*A61B 17/22* (2006.01)
*A61N 7/02* (2006.01)
(Continued)

(52) U.S. Cl.
CPC .... *A61B 17/22022* (2013.01); *A61B 17/2202* (2013.01); *A61B 17/22029* (2013.01);
(Continued)

(58) Field of Classification Search
CPC .............. A61B 17/22; A61B 17/22004; A61B 17/22012; A61B 17/2202; A61B 17/22029; A61B 2017/22001; A61B 2017/22012; A61B 2017/22021; A61B 2017/22025; A61B 2017/22027; A61B 2017/22062; A61B 2017/22081; A61B 2017/22098;
(Continued)

(56) References Cited

U.S. PATENT DOCUMENTS 4,046,150 A    9/1977    Schwartz et al.
4,280,511 A    7/1981    O'Neill
(Continued)

FOREIGN PATENT DOCUMENTS

DE          3038445 A1     5/1982
WO     2012/019230 A1     2/2012

OTHER PUBLICATIONS

International Search Report and Written Opinion received for PCT Patent Application No. PCT/US2014/048794 dated Nov. 5, 2014, 10 pages.

*Primary Examiner* — Jonathan Miles
*Assistant Examiner* — Kendra Obu
(74) *Attorney, Agent, or Firm* — Morrison & Foerster LLP

(57) ABSTRACT

Described here are angioplasty balloon devices for generating shock waves to break up calcified plaques along a length of a vessel and methods of making such devices. Generally, the devices may be used in angioplasty and/or valvuloplasty procedures, but may alternatively be used in other applications. In some variations, the device may include an elongate member, a plurality of electrode assemblies, and at least one tubular sleeve interposed between adjacent or neighboring electrode assemblies that form a continuous outer profile between the electrode assemblies. These devices may have a smooth, continuous outer profile without substantial profile transitions and/or may have stiffening sections between electrode assemblies.

2 Claims, 7 Drawing Sheets

(51) Int. Cl.
*A61B 18/14* (2006.01)
*A61B 17/00* (2006.01)

(52) U.S. Cl.
CPC . *A61B 18/1492* (2013.01); *A61B 2017/00526* (2013.01); *A61B 2017/22025* (2013.01); *A61B 2017/22027* (2013.01); *A61B 2017/22028* (2013.01); *A61B 2017/22062* (2013.01); *A61B 2017/22081* (2013.01); *A61B 2017/22098* (2013.01); *A61B 2018/1405* (2013.01); *A61N 7/022* (2013.01); *Y10T 29/49201* (2015.01)

(58) Field of Classification Search
CPC .......... A61B 5/0422; A61B 2018/1405; A61B 2018/1467; A61B 2018/1497; A61B 18/1492; A61B 17/22022; A61B 2017/00526; A61B 2017/22028; A61N 7/00; A61N 7/02; A61N 7/022; A61N 2007/0004; A61N 2007/0043; A61N 2007/0078; A61N 2007/0095; A61M 11/044; A61M 25/00; A61M 25/0013; A61M 25/0045; A61M 25/0054; A61M 2025/0004; Y10T 29/49201
See application file for complete search history.

(56) References Cited

U.S. PATENT DOCUMENTS

| | | |
|---|---|---|
| 5,269,291 A | 12/1993 | Carter |
| RE35,924 E | 10/1998 | Winkler |
| 5,916,158 A | 6/1999 | Webster, Jr. |
| 6,144,870 A | 11/2000 | Griffin, III |
| 6,176,842 B1 | 1/2001 | Tachibana et al. |
| 6,200,307 B1 * | 3/2001 | Kasinkas ............... A61B 17/22 606/15 |
| 6,440,124 B1 | 8/2002 | Esch et al. |
| 8,747,416 B2 | 6/2014 | Hakala et al. |
| 2001/0041880 A1 | 11/2001 | Brisken et al. |
| 2003/0109812 A1 | 6/2003 | Corl et al. |
| 2009/0312768 A1 | 12/2009 | Hawkins et al. |

* cited by examiner

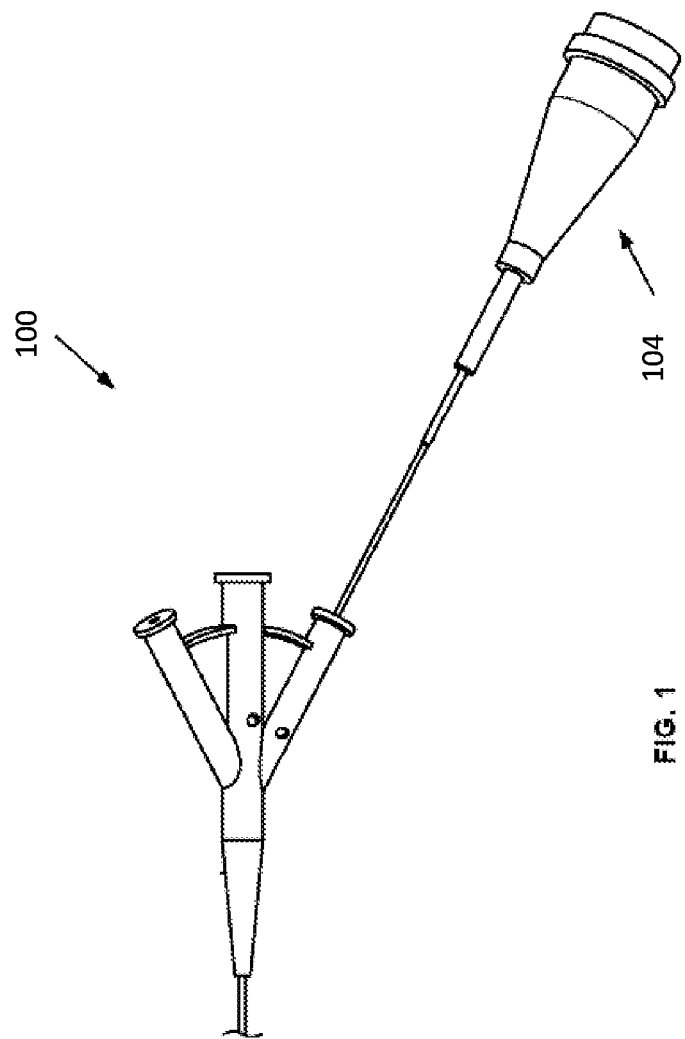
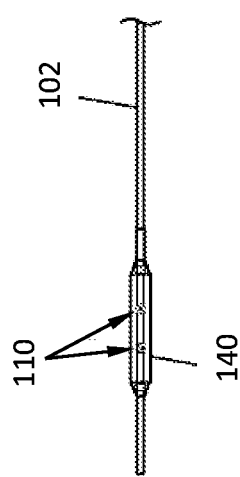
FIG. 1

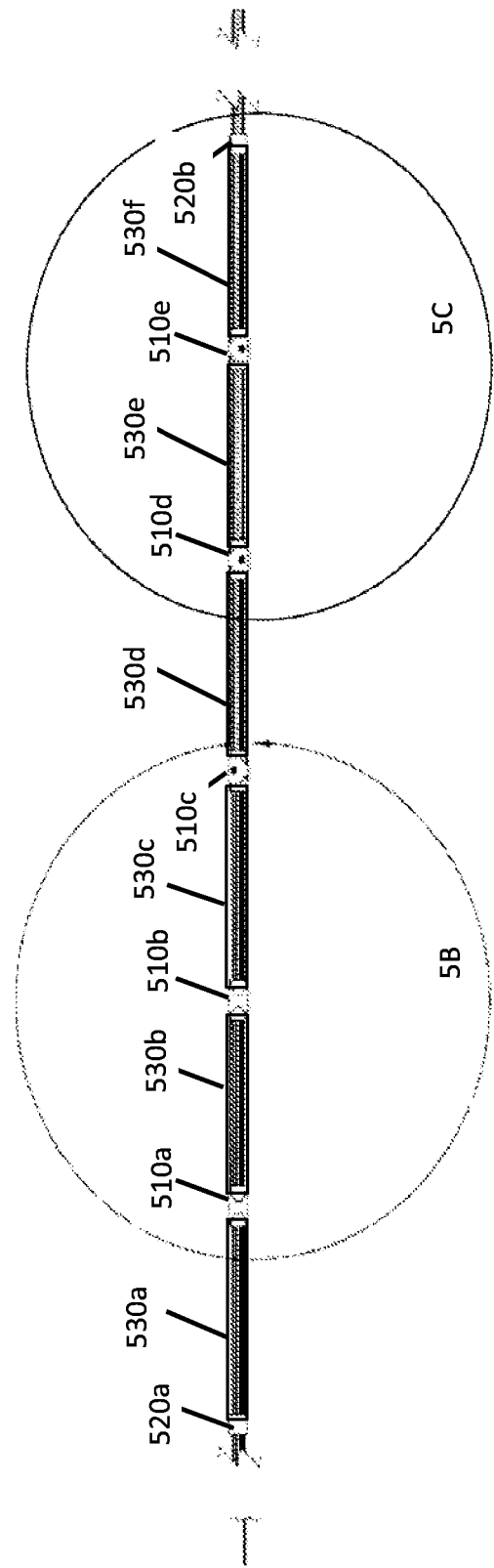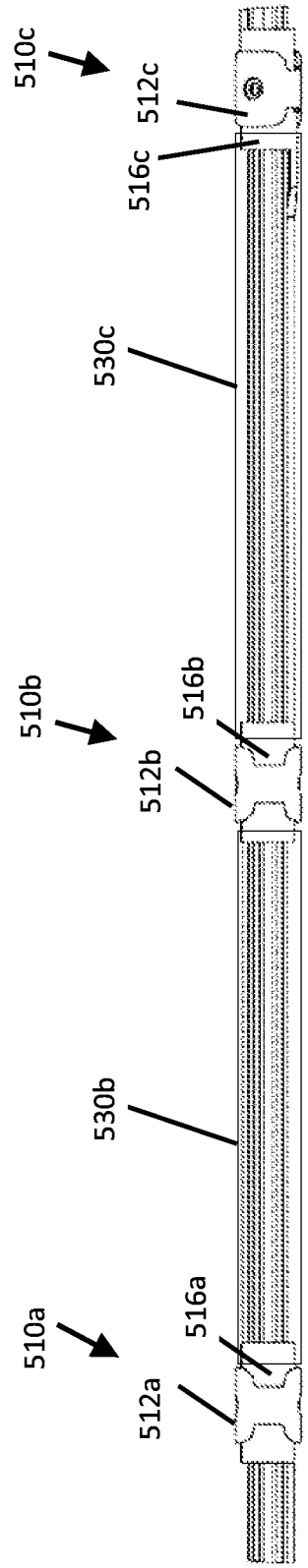
FIG. 5A
FIG. 5B

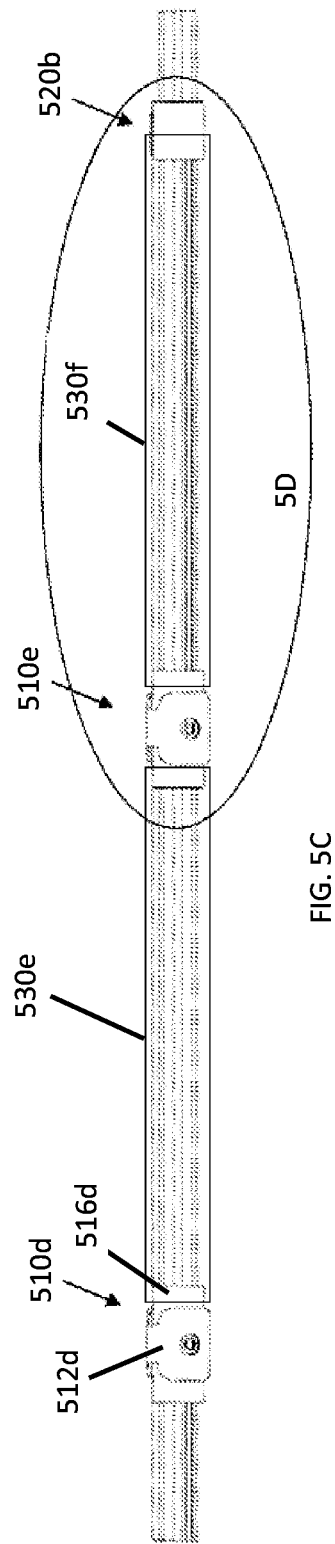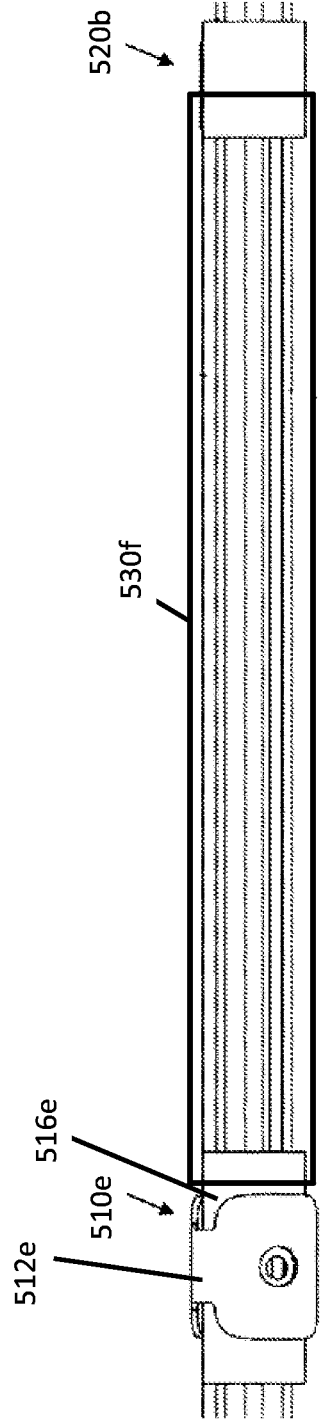
FIG. 5C
FIG. 5D

ANGIOPLASTY BALLOON

CROSS-REFERENCE TO RELATED APPLICATIONS

This application claims priority to U.S. Provisional Patent Application No. 61/860,755, filed on Jul. 31, 2013, and titled "LITHOPLASTY BALLOON", the disclosure of which is incorporated herein by reference in its entirety.

BACKGROUND OF THE INVENTION

Currently, angioplasty balloons are used to open calcified lesions in the wall of an artery. However, as an angioplasty balloon is inflated to expand the lesion in the vascular wall, the inflation pressure stores a tremendous amount of energy in the balloon until the calcified lesion breaks or cracks. That stored energy is then released and may stress and injure the wall of the blood vessel.

Electrohydraulic lithotripsy has been typically used for breaking calcified deposits or "stones" in the urinary or biliary track. Lithotripsy may similarly be useful for breaking calcified plaques in the wall of a vascular structure. Shock waves generated by lithotripsy electrodes may be used to controllably fracture a calcified lesion to help prevent sudden stress and injury to the vessel or valve wall when it is dilated using a balloon. For example, a balloon may be placed adjacent leaflets of a valve to be treated and inflated with a liquid. Within the balloon is an electrode shock wave generator that produces shock waves that propagate through the liquid and impinge upon the valve. The impinging shock waves soften, break, and/or loosen the calcified regions for removal or displacement to open the valve or enlarge the valve opening. Additional improved lithotripsy or balloon shock wave catheters that can readily access and treat various locations in the vasculature for angioplasty and/or valvuloplasty procedures may be desirable.

However, due to its electrodes having a larger diameter than at least some of the catheter body, a balloon shock wave catheter may have difficulty passing through small openings in a stenosis, and may "catch" or hang up on tissue. A balloon shock wave catheter may also suffer from kinking as it navigates through tissue. Thus, there is a need to create an improved balloon shock wave catheter.

BRIEF SUMMARY OF THE INVENTION

Described here are angioplasty balloon devices for generating shock waves to break up calcified plaques along a length of a vessel and methods of making such devices. Generally, the devices may be used in angioplasty and/or valvuloplasty procedures, but may additionally or alternatively be used in other applications. These devices may have a smooth, continuous outer profile without substantial profile transitions and/or may have stiffening sections between electrode assemblies. In some variations, the device comprises an elongate member, a plurality of electrode assemblies, and at least one tubular sleeve interposed between adjacent or neighboring electrode assemblies that form a continuous outer profile between the electrode assemblies. In some variations, the method for making the device comprises providing an elongate member with a plurality of electrode assemblies, placing a first tubular sleeve on the elongate member between two electrode assemblies, placing a second tubular sleeve on the elongate member between two electrode assemblies, and radially shrinking the tubular sleeves such that the tubular sleeves form a continuous outer profile along the electrode assemblies and tubular sleeves.

In some variations, the devices described here comprise an elongate member having a diameter, a first electrode assembly at a first axial location on the elongate member and comprising a first outer sheath, a second electrode assembly at a second axial location on the elongate member and comprising a second outer sheath, a third electrode assembly at a third axial location on the elongate member and comprising a third outer sheath, a first tubular sleeve surrounding the elongate member and axially extending between the first and second electrode assemblies, and a second tubular sleeve surrounding the elongate member and axially extending between the second and third electrode assemblies. Each of the outer sheaths of the electrode assemblies has an outer diameter larger than the diameter of the elongate member. The first tubular sleeve has an outer diameter substantially similar to at least one of the outer diameters of the first and second electrode assemblies. The second tubular sleeve has an outer diameter substantially similar to at least one of the outer diameters of the second and third electrode assemblies. In some variations, the first sleeve overlaps at least a portion of the first electrode assembly and at least a portion of the second electrode assembly. In some variations, the second sleeve overlaps at least a portion of the second electrode assembly and at least a portion of the third electrode assembly. In some variations, at least one of the outer sheaths of the electrode assemblies comprises an electrode. In some variations, at least one of the electrode assemblies comprises a pair of inner electrodes disposed radially across the elongate member from one another and an inner sheath disposed around the inner electrode. In some variations, the outer diameters of the electrode assemblies are substantially equal. In some variations, at least one of the tubular sleeves is radially shrinkable. In some variations, at least one of the tubular sleeves is radially shrinkable upon heat application. In some variations, the device further comprises at least one marker band on the elongate member, where the marker band has a marker band outer diameter larger than the diameter of the elongate member, and a third tubular sleeve surrounding the elongate member and axially extending between one of the electrode assemblies and the marker band, where the third tubular sleeve has an outer diameter substantially similar to the marker band outer diameter.

In some variations of the method for making the devices described here, the method comprises providing an elongate member having at least a first electrode assembly at a first axial location on the elongate member, a second electrode assembly at a second axial location on the elongate member, and a third electrode assembly at a third axial location on the elongate member, where each electrode assembly has an outer sheath having an outer diameter larger than the diameter of the elongate member. The method further comprises placing a first radially shrinkable tubular sleeve on the elongate member between the first and second axial locations; placing a second radially shrinkable tubular sleeve on the elongate member between the second and third axial locations; radially shrinking the first sleeve such that the first sleeve creates a substantially continuous outer profile along the first electrode assembly, the first sleeve, and the second electrode assembly; and radially shrinking the second sleeve such that the second sleeve creates a substantially continuous outer profile along the second electrode assembly, the second sleeve, and the third electrode assembly. In some variations, placing the first sleeve on the elongate member comprises overlapping the first sleeve with at least a portion of the first electrode assembly and overlapping the first sleeve with at least a portion of the second electrode assembly. Additionally or alternatively, in some variations, placing the second sleeve on the elongate member comprises overlapping the second sleeve with at least a portion of the second electrode assembly and overlapping the second sleeve with at least a portion of the third electrode assembly. In some variations, the outer diameter of the first, second, and third electrode assemblies are substantially equal. In some variations, radially shrinking the first sleeve is performed prior to placing the second sleeve on the elongate member. In some variations, radially shrinking the first sleeve is performed after placing the second sleeve on the elongate member. In some variations, radially shrinking the first and/or second sleeve comprises applying heat to the sleeve.

In some variations, the devices described here comprise an elongate member having a diameter, an electrode assembly at a first axial location on the elongate member and comprising an outer sheath, a marker band at a second axial location on the elongate member and having a marker band outer diameter, and a tubular sleeve surrounding the elongate member and axially extending between the electrode assembly and the marker band. The electrode outer sheath has an electrode outer diameter larger than the diameter of the elongate member, and the marker band may or may not have a marker band outer diameter larger than the diameter of the elongate member. At least a portion of the sleeve has an outer diameter substantially similar to at least one of the electrode outer diameter and the marker band outer diameter. In some variations, the device further comprises a second marker band on a third axial location on the elongate member and having a second marker band outer diameter. In some variations, the device may further include a second tubular sleeve surrounding the elongate member and axially extending between the electrode assembly and the second marker band, at least a portion of the second sleeve having an outer diameter substantially similar to at least one of the electrode outer diameter and the second marker band outer diameter. In some variations, the first sleeve overlaps at least a portion of the electrode assembly and at least a portion of the first marker band. In some variations, the second sleeve overlaps at least a portion of the electrode assembly and at least a portion of the second marker band. In some variations, at least one of the first and second marker band outer diameters is less than the electrode outer diameter.

BRIEF DESCRIPTION OF THE DRAWINGS

FIG. 1 shows one variation of an angioplasty balloon shock wave device;

FIG. 5A shows the distal end of another variation of an angioplasty balloon shock wave device having a substantially continuous outer profile;

FIGS. 5B, 5C, and 5D show various detailed views of the variation of the angioplasty balloon shock wave device of FIG. 5A;

DETAILED DESCRIPTION OF THE INVENTION

Figure 2:
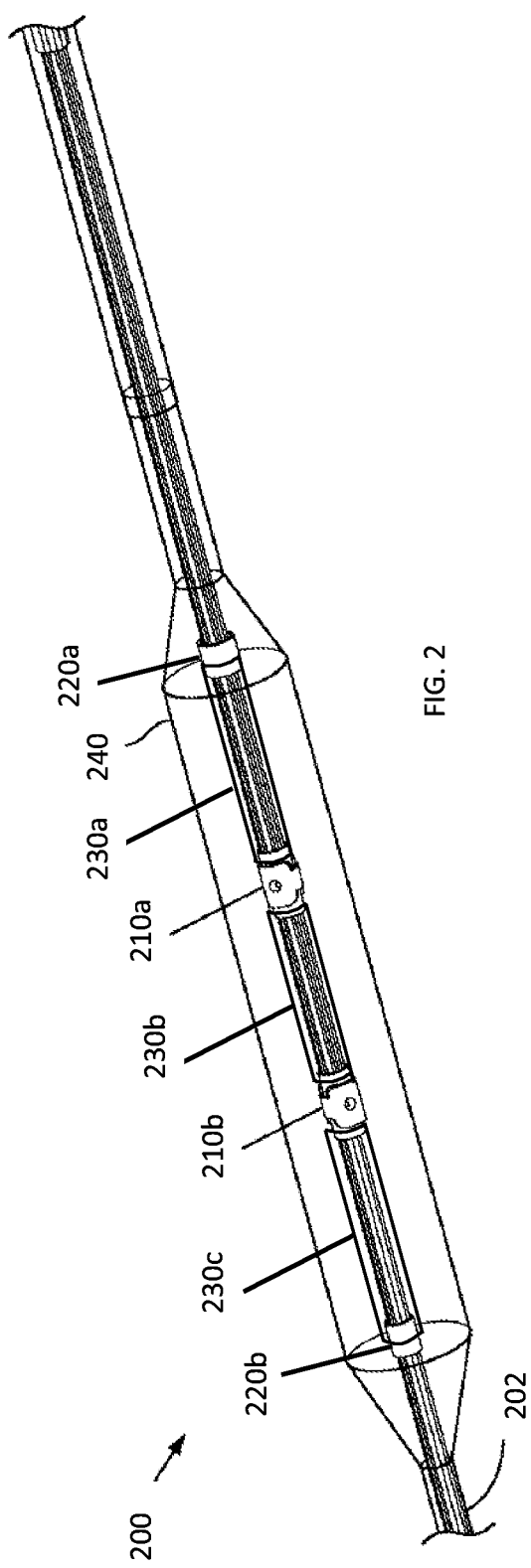
FIG. 2 shows a perspective view of the distal end of a variation of an angioplasty balloon shock wave device having a substantially continuous outer profile within an inflated balloon.

Described herein are methods and systems for angioplasty or shock wave electrodes that may be suitable for use in angioplasty and/or valvuloplasty procedures. However, the shock wave device may additionally or alternatively be used in other suitable applications.

Shock wave electrodes may be sealed within an angioplasty or valvuloplasty balloon that is inflated with a fluid (e.g., saline and/or imaging contrast agent). A shock wave electrode may be attached to a source of high voltage pulses. The voltage pulses may generate a gas bubble at the surface of the electrode and cause a plasma arc of electric current to traverse the bubble and create a rapidly expanding and collapsing bubble, which in turn creates a mechanical shock wave in the balloon. Shock waves may be mechanically conducted through the fluid and through the balloon to apply mechanical force or pressure to break apart any calcified plaques on, or in, the vasculature walls. The size, rate of expansion, and rate of collapse of the bubble (and therefore, the magnitude, duration, and distribution of the mechanical force) may vary. Additional details on shock wave electrode systems and methods of their use may be found in, for example, U.S. Pat. No. 8,747,416 which is incorporated in its entirety by reference.

One example of a shock wave device is depicted in FIG. 1. As shown in FIG. 1, a shock wave device 100 may include a catheter 102, one or more shock wave electrode assemblies 110 arranged at a distal portion of the catheter 102, a high-voltage connector 104 for connecting the shock wave assemblies to a pulse generator, and an angioplasty balloon 140 configured to be inflated with a fluid. There may be any suitable number of electrode assemblies 110 located at the distal end of the catheter 102 and enclosed by the balloon 140, including one, two, three, four, five, or more than five electrode assemblies.

Device for Generating Shock Waves

As shown in FIG. 2, in one variation of a device for generating shock waves, the device 200 includes an elongated member 202, a series of electrode assemblies 210 at respective axial locations on the elongate member, and a series of tubular sleeves 230 surrounding the elongate member. The device may further include one or more marker bands 220 and balloon 240 enclosing the electrode assemblies and/or marker bands. One or more of the tubular sleeves 230 may be placed between a marker band and an electrode assembly neighboring the marker band, or between neighboring electrode assemblies. The device may include any suitable number of electrode assemblies 210, marker bands 220, and tubular sleeves 230. For example, in some variations, the device may include a single electrode assembly, a proximal marker band located proximal to the electrode assembly, a distal marker band located distal to the electrode assembly, a proximal tubular sleeve interposed between the proximal marker band and the electrode assembly, and a distal tubular sleeve interposed between the electrode assembly and the distal marker band. As another example, the device depicted in FIG. 2 includes a first electrode assembly 210a placed at a first axial location on the elongate member, a second electrode assembly 210b placed at a second axial location on the elongate member, a first marker band 220a placed proximal to the first electrode assembly 210a on the elongate member, and a second marker band 220b placed distal to the second electrode assembly 210b. Device 200 further includes three tubular sleeves, including a first sleeve 230a interposed between the marker band 220a and the electrode assembly 210a, a second sleeve 230b interposed between the first electrode assembly 210a and the second electrode assembly 210b, and a third sleeve 230c interposed between the second electrode assembly 210b and the marker band 220b. As another example, the device 300 depicted in FIG. 3 includes five electrode assemblies 310a-e, two marker bands 320a and 320b, and six tubular sleeves 330a-330f. Each axial portion of the catheter between a marker band and electrode assembly, or between neighboring electrode assemblies, is surrounded by a respective tubular sleeve. All electrode assemblies, marker bands, and tubular sleeves are enclosed by balloon 340.

The elongate member is navigable within a tissue body (e.g., a blood vessel) and carries the shock wave electrodes, balloon, and other parts collectively configured to generate a shock wave to a location of treatment. As shown in FIG. 1, the elongate member may include a catheter 102, such as one suitable for use in an angioplasty or valvuloplasty balloon. In some variations, the elongate member may be a catheter with a guidewire lumen. The elongate member may be configured with features to retain at least a portion of one or more electrode assemblies, wires in communication with one or more electrode assemblies, and/or other parts placed on the elongate member. For example, the catheter may include longitudinal grooves to help retain a portion of the electrode assemblies and/or wires. In some variations, the elongate member may include features such as those described in U.S. Pat. No. 8,747,416 referenced above. However, the elongate member may include any structure suitable for carrying the shock wave electrodes and balloon to a location of treatment in a body.

Figure 4:
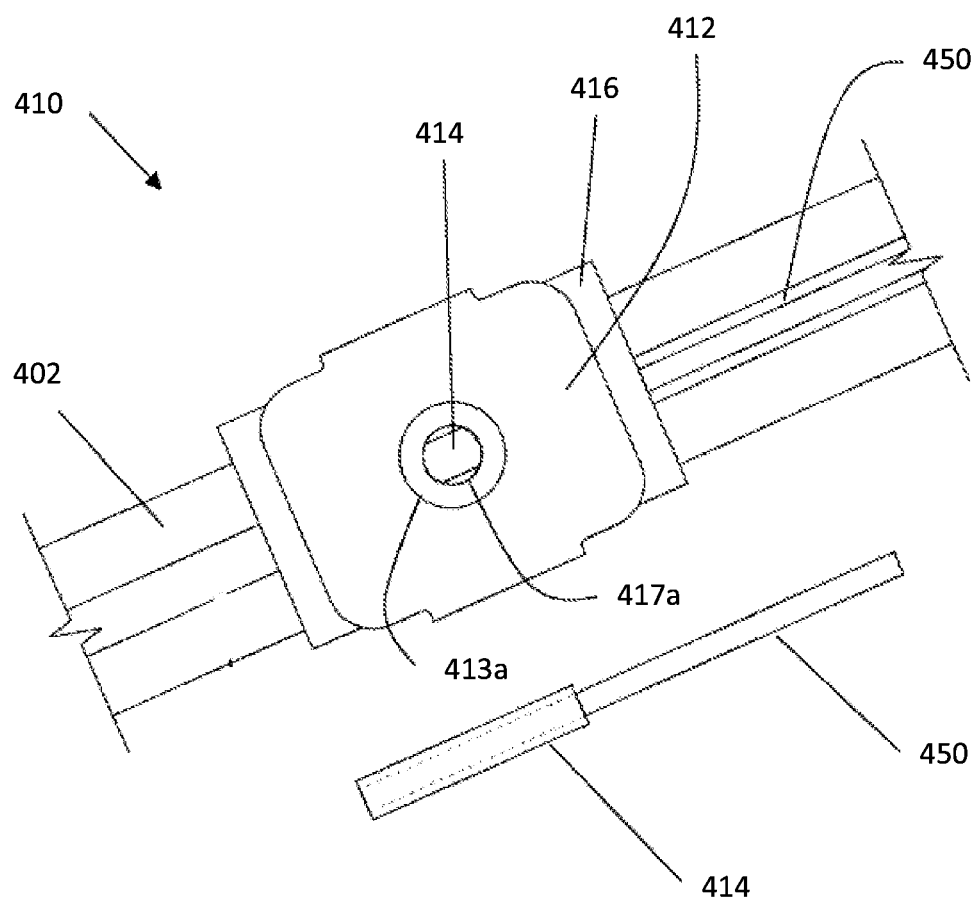
FIG. 4 shows one variation of an insulating sheath of a shock wave electrode assembly.

The electrode assemblies help generate one or more shock waves propagating from the elongate member. Each electrode assembly may be low-profile to navigate and access narrow regions of vasculature. One example of a low-profile electrode assembly is depicted in FIG. 4. The electrode assembly may include a first inner electrode 414, an inner insulating layer or sheath 416 disposed over the first inner electrode and circumferentially wrapped around an elongate member 402 (e.g., a catheter with a guidewire lumen), and an outer electrode sheath 412 disposed over the inner insulating sheath 416. The inner insulating sheath 416 of the electrode assembly 410 may have a first opening 417a that is coaxially aligned over the first inner electrode 414, and the outer electrode sheath 412 may have a first opening 413a that is coaxially aligned over the first opening 417a of the inner insulating sheath. The electrode assembly 410 may also include a second inner electrode that is circumferentially opposite (or otherwise circumferentially and/or axially displaced from) the first inner electrode (and therefore not depicted in the view of FIG. 4). The inner insulating sheath may have a second opening that is coaxially aligned over the second inner electrode, and the outer electrode sheath may have a second opening that is coaxially aligned over the second opening of the inner insulating sheath. A high voltage source can supply a high voltage pulse across the inner electrodes via wires 450 (only one seen in FIG. 4) to generate two shock waves on either side of the assembly. More specifically, an arc will be created across one inner electrode to the outer electrode and across the outer electrode and the remaining inner electrode on the opposite side of the assembly.

Figure 3:
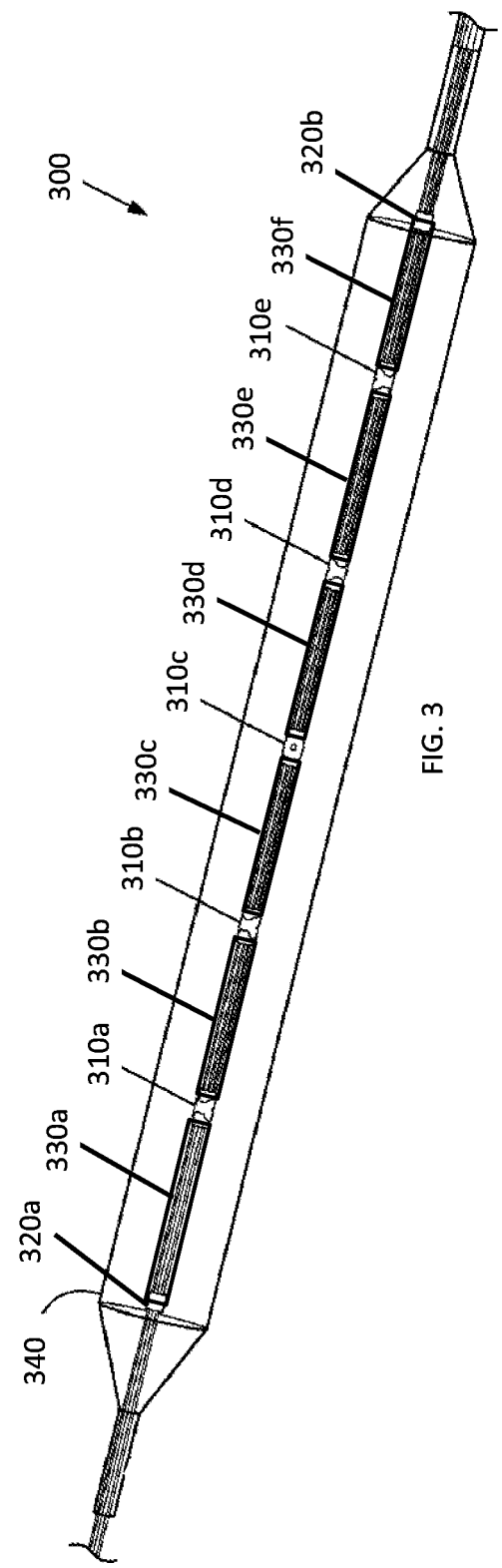
FIG. 3 shows a perspective view of the distal end of another variation of an angioplasty balloon shock wave device having a substantially continuous outer profile within an inflated balloon.

While the insulating sheath is depicted in FIG. 4 as fully circumscribing the elongate member, it should be understood that in other variations, an insulating layer may not fully circumscribe the elongate member. As shown in FIG. 4, the inner insulating sheath 416 may extend further axially (proximally and distally) beyond the edges of the outer electrode sheath 412 so as to form a step down in profile between the outer electrode sheath 412 (having an outer diameter larger than both the diameter of the elongate member and the inner insulating sheath 416) and the inner insulating sheath 416. Furthermore, while the outer electrode sheaths of multiple electrode assemblies are depicted in FIGS. 2 and 3 as having approximately the same outer diameter, it should be understood that in other variations, some or all of the electrode sheaths may differ in outer diameter.

Alternatively, some variations of an electrode assembly may lack an insulating sheath or layer disposed over the elongate member, and may instead comprise an inner electrode having an insulating coating directly applied over the inner electrode. The insulating coating may cover the inner electrode such that a region of the conductive portion of the inner electrode is exposed, while the rest of the inner electrode is covered by the coating. The opening in the outer electrode sheath may be coaxially aligned with the exposed region of the inner electrode. The thickness and/or material of the insulating coating may be varied depending on the magnitude of the voltage to be applied on the electrode. Examples of insulating coatings may be Teflon, polyimide, etc.

As noted above, the electrode assembly of FIG. 4 is configured to generate a pair of shock waves. Similarly, each of the electrode assemblies along the elongate member may be configured to generate a pair of shock waves. In some variations, the series of electrode assemblies generate shock waves that propagate outward from different axial and/or circumferential locations on the elongate member. For example, in the device depicted in FIG. 2, electrode assembly 210a at a first axial location may generate shock waves that propagate from the top and bottom longitudinal sides of the elongate member 202, while the electrode assembly 210b at a second axial location may generate shock waves that propagate from the left and right longitudinal sides of the elongate member 202. In other variations, each electrode assembly may generate a pair of shock waves that propagate outward at the same circumferential location, but from different axial locations along the length of the elongate member. Furthermore, in other variations, the electrode assemblies may be configured and operated as described in U.S. Pat. No. 8,747,416 referenced above, or in any suitable manner.

In some variations, the elongate member further includes one or more marker bands placed at different axial locations along the elongate member. In some variations, a marker band may have an outer diameter that is approximately equal to the diameter of one or more of the electrode assemblies. In some variations, a marker band may have an outer diameter that is greater than or less than one or more of the electrode assemblies. Furthermore, in some variations, a marker band may have an outer diameter that is greater than the diameter of the elongate member, though in some variations a marker band may have an outer diameter that is approximately equal to or less than the diameter of the elongate member (e.g., the marker band lies in a circumferential recess of the elongate member and does not extend radially beyond the external surface of the elongate member).

A marker band may be radiopaque so as to be visible under imaging methods (e.g., fluoroscopy) during the treatment procedure, to allow a practitioner to identify the location and/or orientation of the shock wave device as the device is inserted through the vasculature of the patient. For example, as shown in FIG. 3, device 300 includes a proximal marker band 320a placed proximal to the series of electrode assemblies 310a-e, and a distal marker band 320b placed distal to the series of electrode assemblies 310a-e. In some variations, one or more marker bands may be located proximal to the proximal-most electrode assembly, and/or distal to the distal-most electrode assembly, and/or in the center of the elongate member and/or any other axial location along the length of the elongate member. In some variations, one or more marker bands may act as a common node for wires carrying a return current back to the high voltage pulse generator. The marker band may, for example, be made of tantalum and/or any suitable radiopaque material.

The tubular sleeves provide a substantially continuous outer profile on the elongate member and provide additional structural support and protection for the shock wave device. In particular, the continuous profile provided by the tubular sleeves may help prevent the shock wave device from catching or becoming lodged in the vasculature such as a tight stenosis. Additionally, the continuous profile may help prevent the electrode assemblies from scratching the surrounding balloon when the balloon is deflated, or prevent the electrode assemblies from damaging other portions of the device and/or surrounding vasculature of the patient. Furthermore, the tubular sleeves may provide structural support to the elongate member, stiffening the relatively flexible areas of the elongate member between electrode assemblies (and between electrode assemblies and marker bands) and making those areas less likely to kink at transition zones near the electrode assemblies and marker bands.

As shown in FIGS. 5A-5D, each tubular sleeve may surround a respective axial portion of the elongate member. For instance, as shown in FIG. 5A, tubular sleeve 530a surrounds the axial portion of the elongate member interposed between marker band 520a and the electrode assembly 510a. Tubular sleeve 530b surrounds the axial portion of the elongate member interposed between the electrode assemblies 510a and 510b. Similarly, tubular sleeve 530c, 530d, and 530e surround the axial portions of the elongate member interposed between the electrode assemblies 510b and 510c, between the electrode assemblies 510c and 510d, and between the electrode assemblies 510d and 510e, respectively. Additionally, tubular sleeve 530f surrounds the axial portion of the elongate member interposed between the electrode assembly 510e and 520b.

The number of tubular sleeves may vary depending on the number of electrode assemblies and/or marker bands on the elongate member. In some variations, the shock wave device may include tubular sleeves located in only a subset of axial portions located between neighboring electrode assemblies or between a marker band and a neighboring electrode assembly. Furthermore, although the device as depicted in the figures includes a single tubular sleeve extending between adjacent electrode assemblies and/or marker bands, it should be understood that in other variations the axial portion between adjacent electrode assemblies and/or marker bands may be covered by multiple tubular sleeves. For instance, in some variations two or more tubular sleeves may be placed in tandem along such axial portion (and may or may not overlap one another), such that one tubular sleeve surrounds one part of the axial portion while another tubular sleeve surrounds another part of the axial portion. Additionally or alternatively, in some variations two or more tubular sleeves may be placed in layers around an axial portion of the elongate member. In other words, various combinations of tubular sleeves surrounding the elongate member may result in a substantially continuous outer profile along the electrode assemblies and tubular sleeves.

Each tubular sleeve may overlap with a portion of its adjacent electrode assembly or marker band. In particular, an end of a tubular sleeve may overlap the portion of the inner insulating sheath of an adjacent electrode assembly. In some variations, the tubular sleeve may extend up to and abut the edge of the outer electrode sheath, as depicted by sleeve 530b abutting the edge of the outer electrode sheath 512a in FIG. 5B. In other variations, the tubular sleeve may fall just short of the edge of the outer electrode sheath, leaving a suitably negligible gap (e.g., 0.5 mm, 1 mm) distance between the tubular sleeve and the outer electrode sheath, similar to that depicted by sleeve 530b extending to just short of the outer electrode sheath 512b in FIG. 5B. Similarly, an end of a tubular sleeve may overlap at least a portion of the marker band, and the degree of overlap may vary (e.g., a third of the marker band length, half of the marker band length, two-thirds of the marker band length). The outer diameter of the tubular sleeve may be substantially equal to the outer diameter of an electrode assembly and/or marker band adjacent to the tubular sleeve, so as to provide a substantially continuous outer profile along the electrode assemblies, tubular sleeves, and/or marker bands on the elongate member.

For example, as shown in FIG. 5B, the outer diameter of the tubular sleeve 530b is substantially the same as the outer diameters of the outer electrode sheaths 512a and 512b of adjacent electrode assemblies 510a and 510b, respectively. One end of the sleeve 530b overlaps with the inner insulating sheath 516a of the electrode assembly 510a and abuts the edge of the outer electrode sheath 512a. The other end of sleeve 530b overlaps with the inner insulating sheath 516b of the electrode assembly 510b and nearly abuts the edge of the outer electrode sheath 512b. Similarly, the tubular sleeve 530c overlaps with inner electrode sheath 516b of the electrode assembly 510b until the sleeve nearly abuts the outer electrode sheath 512b, and sleeve 530c overlaps with the inner electrode sheath 516c of the electrode assembly 510c until the sleeve abuts the outer electrode sheath 512c. As shown in in FIG. 5A, tubular sleeve 530d similarly overlaps with portions of the electrode assemblies 510c and 510d. As shown in FIG. 5C, tubular sleeve 530e also similarly overlaps with portions of the electrode assemblies 510d and 510e. As shown in FIGS. 5C and 5D, one end of the tubular sleeve 530f may overlap with inner electrode sheath 516e of the electrode assembly 510e and the other end of the tubular sleeve 530f may overlap with approximately half the length of marker band 520b.

The tubular sleeves may be radially shrinkable to engage with and secure to the elongate member, the electrode assemblies, and/or the marker bands. In its radially compressed state, a tubular sleeve may have an outer diameter substantially equal to the outer diameter of the adjacent electrode assembly and/or adjacent marker band. In one variation, the tubular sleeves are radially shrinkable due to application of heat (i.e., heat shrink tubing). For example, the tubular sleeves may include polyester (e.g., PET) with a strain ratio of approximately 1.3-1.4. The tubular sleeves may additionally or alternatively include PTFE or other suitable material. In other variations, the tubular sleeves are radially shrinkable in other manners, such as crimping (e.g., crimping down longitudinally-oriented peaks and valleys in the tubular sleeves) or by virtue of including elastic material (e.g., the tubular sleeves elastically cling to the elongate member, electrode assemblies, and/or marker bands in a radially compressed state).

In some variations, the tubular sleeves are slipped axially over the elongate member to surround and engage with the elongate member, electrode assemblies, and/or marker bands. However, alternatively, the tubular sleeves may be structured to surround the elongate member in other manners. For instance, in one variation, the tubular sleeve may have a longitudinal slit that opens and closes to permit the tubular sleeve to approach and surround the elongate member from a lateral direction. In another variation, the tubular sleeve may have a helical slit that opens and closes to permit the tubular sleeve from being turned onto the elongate member in a spiral direction. In other variations, the tubular sleeve may have other suitable slits or other openings to permit the tubular sleeve to be installed onto the elongate member. The slit or opening may furthermore be sealed closed after the tubular sleeve is placed onto the elongate member, such as with the application of heat or epoxy, or by virtue of being made of a self-healing polymer or other material. In yet another variation, the tubular sleeve may include putty, foam, or other suitable material that is molded around the elongate member, one or more electrode assemblies, and/or one or more marker bands.

Figure 6:
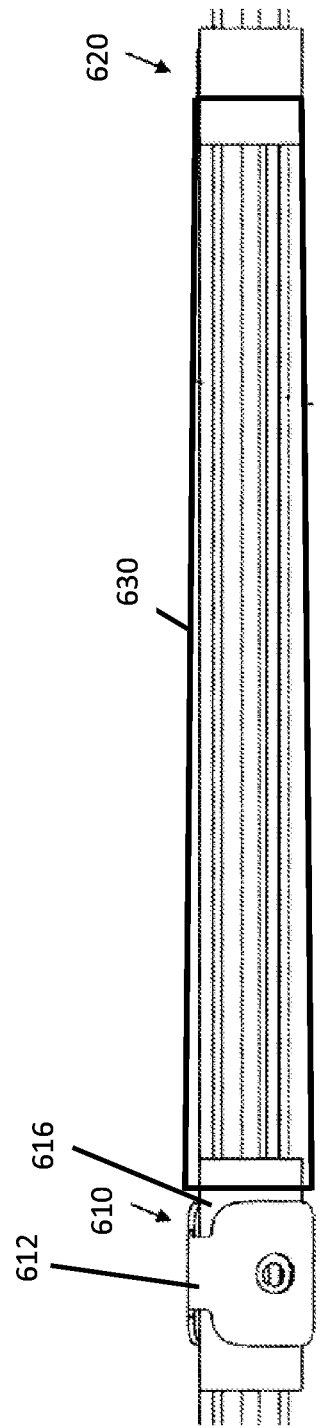
FIG. 6 shows a detailed view of the distal end of another variation of the angioplasty balloon shock wave device.

Although FIGS. 5A-5D depict all of the tubular sleeves 530a-f as being largely similar, it should be understood that some or all of the tubular sleeves may differ in some way. For instance, the tubular sleeve surrounding an axial portion of the elongate member that is adjacent to a marker band may be made of a different material or different diameter, such as to account for the marker band having a different outer diameter than the outer diameter of the electrode assemblies. For example, in some variations, a tubular sleeve (corresponding to sleeve 530a) interposed between the proximal marker band and a first electrode assembly may be made of a different kind of tubing than the tubing used for the other tubular sleeves (corresponding to sleeves 530b-530f). In some variations, the tubular sleeve having an end that is adjacent to either the proximal marker band or the distal marker band may be tapered or flared to accommodate a marker band outer diameter that is smaller or larger, respectively, than the outer diameter of a neighboring electrode assembly. For example, as shown in FIG. 6, sleeve 630 has a tapering outer profile, with one sleeve end overlapping the inner electrode sheath 616 of electrode assembly 610, and another sleeve end overlapping the marker band 620. Marker band outer diameter 620 is less than the diameter of outer electrode sheath 612, and sleeve 630 has an outer profile that tapers from the electrode assembly 610 to the marker band 620. In other variations, the tubular sleeve maintains a consistent diameter throughout its length regardless of whether it is placed between two electrode assemblies or between an electrode assembly and a marker band.

Additionally, the length and other dimensions of the tubular sleeves may differ based on the distance between electrode assemblies (or between an electrode assembly and a marker band) and the relative diameters of the elongate member, inner insulating sheaths of the electrode assemblies, and outer electrode sheaths of the electrode assemblies. For instance, wall thickness of the tubular sleeve 530b may depend on the difference between the outer diameters of outer electrode sheath 512a and inner insulating sheath 516a, and/or the difference between the outer diameters of outer electrode sheath 512b and inner insulating sheath 516b, in order for the wall thickness to provide a continuous outer profile by overlapping the inner insulating sheaths 516a and 516b and mating smoothly with the outer electrode sheaths 512a and 512b. In one variation, in a shock wave device with five electrode assemblies spaced by a center-to-center distance of approximately 10 mm, each tubing sleeve to be placed between neighboring electrode assemblies may be approximately 9 mm long, to sufficiently overlap with the inner sheaths of the electrode assemblies while ensuring that the outer electrode sheaths are exposed.

In one variation described here for illustrative purposes, the shock wave device may include a catheter, five electrode assemblies arranged at spaced-apart, respective axial locations on the distal end of the catheter, and tubular sleeves interposed between neighboring pairs of electrode assemblies. The catheter alone may have an outer diameter of approximately 0.035 inch (or radius of approximately 0.0175 inch). Each electrode assembly may have two inner electrodes on opposite sides of the elongated catheter, an insulating sheath layer disposed around the inner electrodes, and an outer electrode sheath disposed around the insulating sheath layer. Each inner electrode may have a thickness of approximately 0.001 inch to approximately 0.01 inch (e.g., 0.0015 inch). The insulating sheath may have a thickness of approximately 0.001 inch to approximately 0.006 inch (e.g., 0.0015 inch). The outer electrode sheath may have a thickness of approximately 0.001 inch to approximately 0.03 inch (e.g., 0.0015 inch). To achieve a substantially continuous outer profile between the electrode assemblies, each tubular sleeve may have a wall thickness of approximately 0.0015 inch to make up the difference between the outer diameter of the inner insulating sheath and the outer diameter of the outer electrode sheath. However, in other variations, the catheter, inner electrodes, inner insulating sheath, tubing sleeve, and outer electrode sheath may have any suitable dimensions (e.g., inner diameter, outer diameter, wall thickness).

The balloon may be configured to be filled with a fluid to sealably enclose the electrode assemblies and/or marker bands. FIG. 2 depicts one variation in which the balloon 240 is configured to enclose two electrode assemblies and two marker bands. Similarly, FIG. 3 depicts another variation in which the balloon 340 is configured to enclose five electrodes and two marker bands. The fluid within the balloon may be a conductive fluid, such as saline or an imaging contrast agent, in which shock waves emitted from one or more electrode assemblies may propagate. The balloon may be made of an electrically insulating material that may be rigid (e.g., PET), semi-rigid (e.g., PBAX, nylon, PEBA, polyethylene) or flexible (e.g., polyurethane, silicone). The length of the balloon may vary depending on the number of electrode assemblies and the spacing between each of the electrode assemblies. For example, a balloon for a shock wave device with two electrode assemblies spaced about 7 mm apart (e.g., 6.7 mm) may have a length of about 20 mm. As another example, a balloon for a shock wave device with five electrode assemblies spaced about 10 mm apart may have a length of about 60 mm. In some embodiments, the balloon may be similar to that described in U.S. Pat. No. 8,747,416 referenced above.

Method for Making a Device for Generating Shock Waves

In one variation of a method for making a device for generating shock waves, the method generally includes providing an elongate member with a series of electrode assemblies at respective axial locations on the elongate member, placing a tubular sleeve on the elongate member between adjacent pairs of electrode assemblies, and radially shrinking the tubular sleeves so as to create a substantially continuous outer profile along the electrode assemblies and tubular sleeves. The method may further include surrounding the elongate member, electrode assemblies, and tubular sleeves with a balloon (e.g., an angioplasty or valvuloplasty balloon) filled with a conductive fluid such as saline and/or image contrast fluid. The continuous profile provided by the tubular sleeves may help prevent the shock wave device from catching or becoming lodged in the vasculature such as a tight stenosis. Additionally, the continuous profile may help prevent the electrode assemblies from scratching the balloon when the balloon is deflated, and from damaging other portions of the device and/or surrounding vasculature of the patient. Furthermore, the tubular sleeves may provide structural support to the elongate member, stiffening the relatively flexible areas of the elongate member between electrode assemblies (and between electrode assemblies and marker bands) and making those areas less likely to kink at transition zones near the electrode assemblies and marker bands.

Providing an elongate member may include providing an elongate member as described above. In particular, the elongate member may include at least a first electrode assembly at a first axial location on the elongate member, a second electrode assembly at a second axial location on the elongate member, and a third electrode assembly at a third axial location on the elongate member. Furthermore, each of the electrode assemblies may have an outer sheath (e.g., an outer electrode sheath) having an outer diameter larger than the diameter of the elongate member. In some variations, the elongate member may include any suitable number of electrode assemblies, such as one, two, three, four, five, or more than five. As described previously, in some variations the elongate member may further include one or more marker bands. In some variations, the elongate member is similar to that described in U.S. Pat. No. 8,747,416 referenced above.

Placing the tubular sleeves on the elongate member between adjacent pairs of electrode assemblies arranges the tubular sleeves such that the tubular sleeves are configurable to form a substantially continuous outer profile along the electrode assemblies and tubular sleeves. For example, this step may include placing a first tubular sleeve on the elongate member between the first and second axial locations of the first and second electrode assemblies, respectively, and placing a second tubular sleeve on the elongate member between the second and third axial locations of the second and third electrode assemblies, respectively. In some variations, the method may include placing the tubular sleeves between a marker band and an electrode assembly adjacent to the marker band. Fewer or more tubular sleeves may be placed, depending on the number of electrode assemblies and/or marker bands on the elongate member.

In some variations, placing a tubular sleeve on the elongate member includes overlapping the tubular sleeve with at least a portion of one or more adjacent electrode assemblies, and/or overlapping the tubular sleeve with at least a portion of a marker band. For example, placing the first sleeve on the elongate member may include overlapping the first sleeve with at least a portion of the first electrode assembly and overlapping the first sleeve with at least a portion of the second electrode assembly. Similarly, placing the second sleeve on the elongate member may include overlapping the second sleeve with at least a portion of the second electrode assembly and overlapping the second sleeve with at least a portion of the third electrode assembly. In one variation, the portion of each electrode assembly that is overlapped by the tubular sleeve is a portion of the inner insulation sheath of the electrode assembly (e.g., inner sheath 516 in FIGS. 5B-5D). The extent of overlap between a tubular sleeve and an electrode assembly may vary. For example, as best shown in FIG. 5B, the tubular sleeve 530*b* may cover a maximum or near-maximum amount of the exposed portion of the inner insulation sheath 516*a*, such that the tubular sleeve 530*b* abuts, but does not cover, the outer electrode sheath 512*a*. As another example, as shown in FIG. 5B, there may be a negligible gap (e.g., 0.5 mm, 1 mm) gap between the edges of the tubular sleeve 530*b* and the outer electrode sheath 512*b*. Similarly, the extent of overlap between a tubular sleeve and a marker band may vary (e.g., a third of the marker band length, half of the marker band length, two-thirds of the marker band length).

In some variations, the tubular sleeve may be placed onto the elongate member from an axial direction. In some variations, depending on the structure of the tubular sleeve, the tubular sleeve may be placed onto the elongate member in other manners, such as from a lateral direction (such as if the tubular sleeve has a longitudinal slit) or a spiral direction (such as if the tubular sleeve has a helical slit). Additionally, any slits in the tubular sleeves may be closed after tubular sleeve placement, such as with epoxy, heat, or by virtue of including a self-healing material.

In some variations, the tubular sleeves are precut to an appropriate length corresponding to the distance between electrode assemblies or between a marker band and a neighboring electrode assembly, such that each precut sleeve may be placed and prepared for fixation on the elongate member without the need for further action. For example, in a shock wave device with electrode assemblies spaced by a center-to-center distance of approximately 10 mm, each tubing sleeve to be placed between neighboring electrode assemblies may be precut to be approximately 9 mm long, with a tolerance of approximately 1 mm, to sufficiently overlap with the inner sheaths of the electrode assemblies while ensuring that the outer electrode sheaths are exposed. In other variations, one or more of the tubular sleeves may be cut to the appropriate length after being placed on the elongate member.

Radially shrinking the tubular sleeves creates a substantially continuous outer profile along the electrode assemblies, tubular sleeves, and/or marker bands. For instance, referring to FIG. 5A as an example, radially shrinking the sleeve 530*a* may create a substantially continuous outer profile along the marker band 520*a*, the sleeve 530*a*, and electrode assembly 510*a*. Radially shrinking the sleeve 530*b* may create a substantially continuous outer profile along the electrode assembly 510*a*, the sleeve 530*b*, and the electrode assembly 510*b*. Similar formation of a continuous outer profile may be achieved by radially shrinking the other tubular sleeves 530*c-f*.

In some variations, radially shrinking the tubular sleeves includes applying heat to one or more of the tubular sleeves. Heat may be applied with a heat gun that emits hot air, a soldering iron, or other suitable instrument. The temperature and duration of heat application may vary depending on the material and dimensions of the tubular sleeves, as well as the degree to which radial shrinkage must occur to properly form a continuous outer profile and/or secure the tubular sleeve to the elongate member. In one variation, radially shrinking the tubular sleeves includes applying to the tubular sleeves hot air at a temperature of 350 degrees Fahrenheit. However, any suitable temperature and duration of heat application may be used to radially shrink the tubular sleeves. In some variations, the tubular sleeves may be radially shrunk in other manners, such as radially crimping with a mechanical vise or other tool. In other variations, the tubular sleeve may include a material that inherently experiences radial shrinkage, such as an elastic material.

Multiple tubular sleeves may be placed and/or radially shrunk on the elongate member in different orders relative to one another. In some variations, some tubular sleeves may be both placed and radially shrunk before other tubular sleeves are placed (e.g., radially shrinking a first sleeve is performed prior to placing a second sleeve on the elongate member). In other variations, some tubular sleeves may not be radially shrunk until other tubular sleeves are placed on the elongate member (e.g., radially shrinking a first sleeve is performed after placing a second sleeve on the elongate member). In yet other variations, some of the tubular sleeves are radially shrunk substantially simultaneously after their placement on the elongate member. Furthermore, the method may include any combination and permutation of the steps of placing and radially shrinking each of the tubular sleeves.

It will be understood that the foregoing is only illustrative of the principles of the invention, and that various modifications, alterations, and combinations can be made by those skilled in the art without departing from the scope and spirit of the invention. Any of the variations of the various shock wave devices disclosed herein can include features described by any other shock wave devices or combination of shock wave devices herein. Furthermore, any of the methods can be used with any of the shock wave devices disclosed. Accordingly, it is not intended that the invention be limited, except as by the appended claims. For all of the variations described above, the steps of the methods need not be performed sequentially.

What is claimed is:

1. A device for generating shock waves comprising:
an elongate member having a diameter;
a first electrode assembly at a first axial location on the elongate member and comprising a first inner sheath surrounded by a first outer sheath, with the diameter of the first outer sheath being larger than the diameter of the elongated member, and wherein the length of the first inner sheath is greater than the length of the first outer sheath such that the ends of the first inner sheath extend beyond the ends of the first outer sheath;
a second electrode assembly at a second axial location on the elongate member and comprising a second inner sheath surrounded by a second outer sheath, with the diameter of the second outer sheath being substantially the same as the diameter of the first outer sheath, wherein the length of the second inner sheath is greater than the length of the second outer sheath such that the ends of the second inner sheath extend beyond the ends of the second outer sheath; and
a tubular sleeve surrounding the elongate member and axially extending between the first and second outer sheaths and covering at least a portion of the first and second inner sheaths along the ends thereof that extend beyond the first and second outer sheaths, the tubular sleeve having an outer diameter substantially similar to the outer diameter of the first outer sheath, said tubular sleeve being radially shrinkable to create a substantially continuous outer diameter along the length of the elongate member.

2. The device of claim 1 wherein the outer sheaths are electrically conductive and the inner sheaths are insulators.

* * * * *